United States Patent
Kulkarni et al.

(10) Patent No.: US 7,781,480 B2
(45) Date of Patent: Aug. 24, 2010

(54) INDOLE DERIVATIVES AND THEIR METAL CONJUGATES AND USES THEREOF

(75) Inventors: Sudhir Appajl Kulkarni, Pune (IN); Supreet Deshpande, Pune (IN)

(73) Assignee: VLife Sciences Technologies Pvt. Ltd., Pune (IN)

( * ) Notice: Subject to any disclaimer, the term of this patent is extended or adjusted under 35 U.S.C. 154(b) by 0 days.

(21) Appl. No.: 11/891,665

(22) Filed: Aug. 10, 2007

(65) Prior Publication Data

US 2008/0242652 A1    Oct. 2, 2008

(30) Foreign Application Priority Data

Mar. 27, 2007    (IN) .................. 565/MUM/2007

(51) Int. Cl.
*A61K 31/404* (2006.01)
*C07D 209/04* (2006.01)

(52) U.S. Cl. ..................... 514/415; 548/483

(58) Field of Classification Search ................. 514/415; 548/483
See application file for complete search history.

(56) References Cited

FOREIGN PATENT DOCUMENTS

WO    WO 00/04903    *    2/2000    ................ 548/200

OTHER PUBLICATIONS

"Cancer." National Cancer Institute Online. Retrieved via Internet [Aug. 16, 2008] URL: http://www.cancer.gov/cancertopics/druginfo/alphalist.*
Shimazaki, Yuichi. Metal Complexes involving indole rings: Structures and effects of metal-indole interactions. Coordination Chemistry Reviews. 253 (2009) 479-492.*

* cited by examiner

*Primary Examiner*—Kamal A Saeed
*Assistant Examiner*—Samantha L Shterengarts
(74) *Attorney, Agent, or Firm*—Crowell & Moring LLP

(57) ABSTRACT

Provided are compounds which are indole derivatives, as well as pharmaceutical compositions containing the compounds. Also provided are methods of using the indole compounds for preventing or treating a disease, or a condition that predisposes to a disease, wherein the disease or condition is associated with activation of the serine/threonine kinase B (Akt) in an animal. The method comprises administering to the animal a preventive or treatment effective amount of the indole compound. Further provided is a method for increasing apoptosis of an animal cell comprising contacting the cell with the indole compound.

3 Claims, No Drawings

INDOLE DERIVATIVES AND THEIR METAL CONJUGATES AND USES THEREOF

FIELD OF THE INVENTION

The invention relates to indole derivatives and their metal conjugates and their use in the treatment of diseases or conditions associated with activation of serine/threonine kinase B (Akt).

BACKGROUND OF THE INVENTION

There is a great need to find effective drugs for variety of high prevalence cancers, e.g., breast cancer, prostrate cancer and complicated cancers such as the pancreatic cancers. In the United States, the prevalence of these cancer types is: breast—2,369,036; prostate—1,937,798 and pancreas—27,688. The incidences reported in 2006 in the United States for these cancers are: breast—180,510; prostate—218,890; pancreas—37,170.

Among the aforementioned cancer types, patients with pancreatic cancer have a high mortality rate. Treatment of pancreatic cancer is rarely successful because this disease has usually metastasized widely by the time it is diagnosed. Therapy consists of surgery and, possibly, radiation and chemotherapy. Presently, there is no approved drug designed exclusively for pancreatic cancer and drugs used in other cancer conditions are now prescribed for pancreatic cancer patients; e.g., gemcitabine is currently used to treat pancreatic cancer. There are several clinical trials underway for pancreatic cancer using various drug combinations.

One of the main causative factors of cancer is defects in the apoptotic pathways (Korsmeyer, *Blood* 80: 879-886, 1992; Hager et al., *Ann. N.Y. Acad. Sci.*, 887: 150-163, 1999). These defects arise out of a loss of regulatory controls as a result of altered gene dosages via gene mutation, deletion or duplication either in autocrine growth signals involved in cell-to-cell communication (e.g., EGF, TNF, NF1, Wnt), or in cell-cycle control factors (e.g., p53 or ABL), or an increase in oncogenes such as Ras, PKB or ABL (Harris, *IUBMB Life* 55: 117-126, 2003).

In most of the aforementioned cancers it has been shown that there is an overexpression of epidermal growth factor receptor (EGFR) leading to activation of the Akt and NF-κB signalling pathways, suggesting that these pathways are important targets. It has been shown that Akt can inhibit death by apoptosis induced by various stimuli in a certain number of cell types and in tumor cells. In accordance with these findings, it has been shown that Akt can, via phosphorylation of given serine residues, inactivate BAD, GSK3.beta., caspase-9 and Forkhead transcription factor, and activate IKKalpha and e-NOS. Various experimental data suggest that the activation of EGFR leads to the activation of Akt which in turn activates NF-κB and, hence, strategies to disrupt this pathway or down regulate EGFR/NF-κB may be useful for achieving maximal therapeutic response in these cancers.

Epidemiological surveys have provided evidence that consumption of certain phytochemicals through diets/specific foods is associated with reduced risk of several types of cancers (Ghaneh et al., *J. Hepatobiliary Pancreat Surg.*, 9: 1-11, 2002; Lee et al., *Cancer Epidemol. Biomarkers Pren.*, 12: 665-668, 2003; Mukhtar et al., *Toxicol. Sci.*, 52: 111-117, 1999). These phytochemicals generally act as competitive inhibitors of ATP and/or non-competitive inhibitors with substrate molecules. However, they are of little use in themselves since they are broad range inhibitors and are effective only when used at high concentrations. On the other hand they can prove to be valuable as models in designing synthetic molecules that can disrupt the phosphorylation reactions as well as signal transduction processes. Thus, synthetic manipulations of certain phytochemicals may be beneficial for evolving highly efficient and selective therapeutic agents, particularly those targeting specific proteins in signal transduction processes.

The majority of oncogenic cell-cycle control factors belong to one of the several families of protein kinases, which are involved in a number of key cell survival, growth and proliferation signal transduction pathways. These can be roughly divided into two major types: protein tyrosine kinases and serine/threonine protein kinases. Among these, Akt signaling is an important signal transduction pathway in cells. Akt is also referred to as protein knase B (PKB), which plays a critical role in controlling the balance between cell survival and apoptosis (Levitz et al., *Science*, 267: 1782-1788, 1995). Akt contains an amino terminal pleckstrin homology (PH) domain that binds phosphorylated lipids at the membrane in response to activation of PI3 kinases. Akt may be activated by insulin and various growth and survival factors through activation of PI3 kinase (Franke et al., *Cell*, 88: 435-437, 1997; Burgeving et al., *Nature*, 376: 599-602, 1995). Binding of growth factors to their receptors activates PI-3K, comprised of 85 kDa and 110 kDa subunits. PI-3K converts phosphatidylinositol-4,5-bisphosphate (PIP2) to PIP3, while the lipid phosphatase PTEN reverts this reaction. PKB binds to PIP3 via its PH domain, where it is phosphorylated on two key residues by upstream kinases. Akt is activated by phospholipid binding and phosphorylation at Thr308 by PDK1 (Franke et al., *Cell*, 727-736, 1995), and also by phosphorylation within the C-terminus at Ser473 by PDK2. PDK1 is localized to the plasma membrane via high-affinity binding of its PH domain to basal levels of PIP3. Following phosphorylation at the plasma membrane, activated PKB translocates to the cytosol, where it is dephosphorylated and inactivated by PP2A. Akt promotes cell survival by inhibiting apoptosis by its ability to phosphorylate and inactivate several targets including Bad, Forkhead transcription factors and caspase-9, all of which are involved in the apoptotic pathway (Alessi et al., *EMBO J.*, 15: 6541-6551, 1996; Brunet et al., *Cell*, 96, 857-868, 1999; Rommel et al., *Science*, 286: 1738-1741, 1999). Recent reports showed that Akt also regulates the NF-κB pathway via phosphorylation and activation of molecules in the NF-κB pathway (Romashkova et al., *Nature*, 401, 86-90, 1999; Nozes et al., *Nature*, 401: 82-85, 1999).

Akt plays an important role in cancer pathologies. The amplification and/or overexpression of Akt has been reported in many human tumors, for instance gastric carcinoma (amplification of AKT1), ovarian, breast or pancreatic carcinomas (amplification and overexpression of AKT2) and breast carcinomas deficient in estrogen receptors, and also androgen-independent prostate carcinomas (overexpression of AKT3). Furthermore, Akt is constitutively activated in all PTEN (−/−) tumors, the phosphatase PTEN being deleted or inactivated via mutations in many types of tumors, for instance ovarian, prostate and endometrial carcinomas, glioblastomas and melanomas. Akt is also involved in the oncogenic activation of bcr-abl (Sarkar et al., *Toxicol. Appl. Pharmacol.*, In Press, 2006; Khawaja, *Nature*, 401: 33-34, 1999; Cardone et al., *Nature*, 282: 1318-1321, 1998; Kitada et al., Am. J. Pathol., 152: 51-61, 1998; Mazure et al., Blood, 90: 3322-3331, 1997; Zhong et al., Cancer Res., 60: 1541-1545, 2000).

SUMMARY OF THE INVENTION

In one embodiment, compounds corresponding to the following structure are provided.

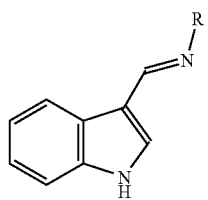
(I)

wherein R is selected from

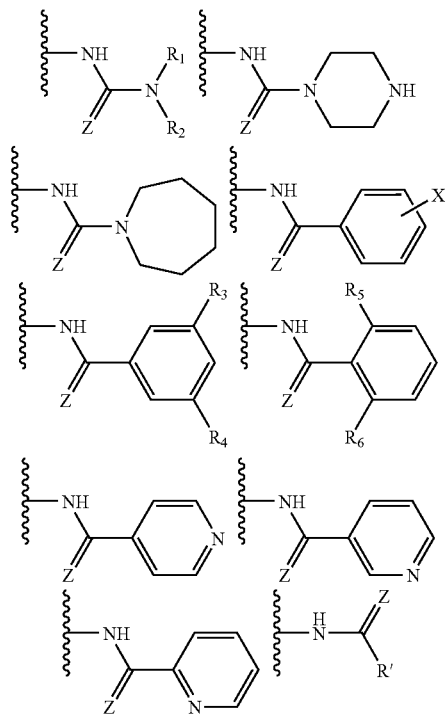

wherein Z is oxygen or sulfur;

wherein $R_1$ and $R_2$ are each independently selected from hydrogen, $(C_1-C_6)$alkyl, $(C_3-C_7)$cycloalkyl, or phenyl;

wherein X is selected from hydrogen, $(C_1-C_4)$alkyl, hydroxyl, $(C_1-C_4)$alkoxy, fluorine, chlorine, bromine, iodine, nitro, or amino;

wherein $R_3$, $R_4$, $R_5$ and $R_6$ are each independently selected from hydrogen or $(C_1-C_4)$ alkyl;

wherein R is selected from $(C_1-C_6)$alkyl, $(C_3-C_7)$cycloalkyl, $(C_1-C_4)$alkoxy, $(C_1-C_3)$haloalkyl, —CH$_2$CN, —CH$_2$—CH(NH$_2$)(COOH), —CH(CH$_2$CH$_2$Cl)$_2$, —O—CH$_2$-Ph, —CH$_2$-Ph, 3-indolyl, 5-indolyl, 7-indolyl, 2-pyrazolyl, 3-pyrazolyl, 2-pyrimidinyl, 4-pyrimidinyl, 5-pyrimidinyl, purine,

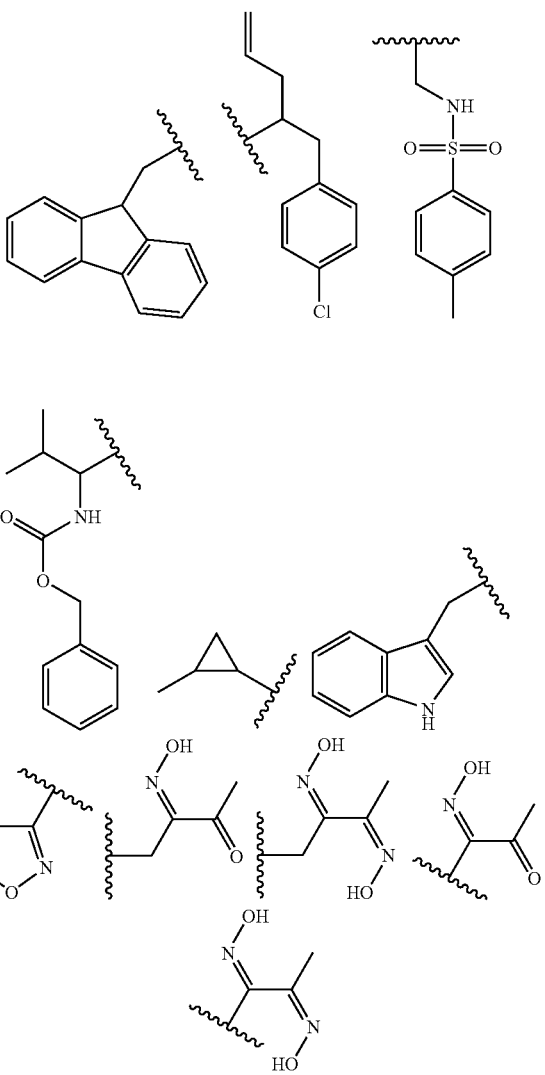

where Ph is phenyl. The compounds also include the corresponding metal conjugates, and pharmaceutically acceptable salts of the compounds and metal conjugates.

In another embodiment, a composition is provided comprising a pharmaceutically acceptable dilutent, carrier or excipient and a compound as described above.

In another embodiment, a method is provided for preventing or treating a disease, or a condition that predisposes to a disease, wherein the disease or condition is associated with activation of the serine/threonine kinase B (Akt) in an animal. The method comprises administering to the animal a preventive or treatment effective amount of a compound as described above.

In yet another embodiment, a method is provided for increasing apoptosis of an animal cell comprising contacting the cell with a compound as described above.

Other methods, features and advantages of the present invention will be or become apparent to one with skill in the art upon examination of the following detailed descriptions. It is intended that all such additional methods, features and advantages be included within this description, be within the scope of the present invention, and be protected by the accompanying claims.

DETAILED DESCRIPTION OF THE INVENTION

Before the present compositions and methods are described, it is to be understood that the invention is not limited to the particular methodologies, protocols, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The terms "disorder," "disease," and "condition" are used inclusively and refer to any status deviating from normal.

The term "alkyl" refers to saturated, monovalent hydrocarbon radicals having straight or branched chains.

The term "cycloalkyl" refers to cyclic ring-containing hydrocarbon moieties containing 3 to 7 carbon atoms.

The term "alkoxy" refers to O-alkyl groups.

The term "haloalkyl" refers to alkyl groups further bearing one or more halogen substituents, e.g., —$CH_2Cl$, —$CH_2CH_2Cl$.

Compounds of the present invention are indole compounds corresponding to Formula (I):

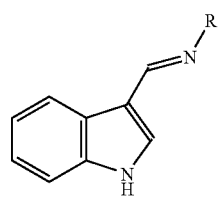

(I)

wherein R is selected from

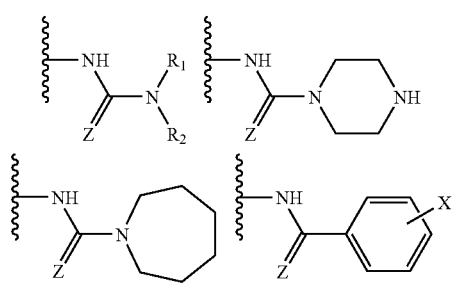

-continued

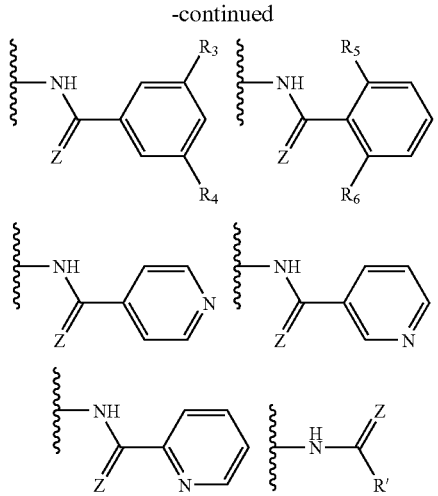

wherein Z is oxygen or sulfur;

wherein $R_1$ and $R_2$ are each independently selected from hydrogen, ($C_1$-$C_6$)alkyl, ($C_3$-$C_7$)cycloalkyl, or phenyl;

wherein X is selected from hydrogen, ($C_1$-$C_4$)alkyl, hydroxyl, ($C_1$-$C_4$)alkoxy, fluorine, chlorine, bromine, iodine, nitro, or amino;

wherein $R_3$, $R_4$, $R_5$ and $R_6$ are each independently selected from hydrogen or ($C_1$-$C_4$)alkyl;

wherein R' is selected from ($C_1$-$C_6$)alkyl, ($C_3$-$C_7$)cycloalkyl, ($C_1$-$C_4$)alkoxy, ($C_1$-$C_3$)haloalkyl, —$CH_2CN$, —$CH_2$—$CH(NH_2)(COOH)$, —$CH(CH_2CH_2Cl)_2$, —O—$CH_2$-Ph, —$CH_2$-Ph, 3-indolyl, 5-indolyl, 7-indolyl, 2-pyrazolyl, 3-pyrazolyl, 2-pyrimidinyl, 4-pyrimidinyl, 5-pyrimidinyl, purine,

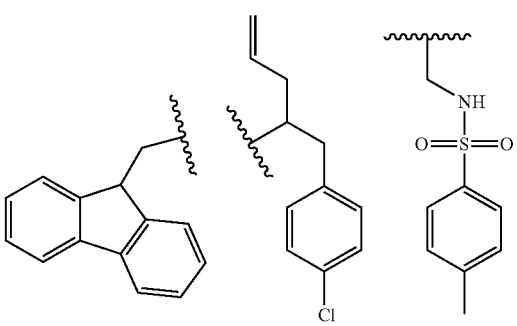

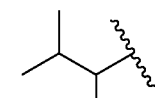

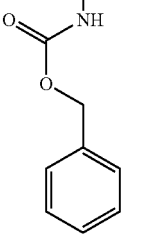

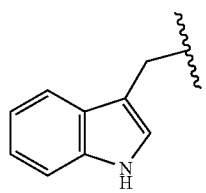

-continued

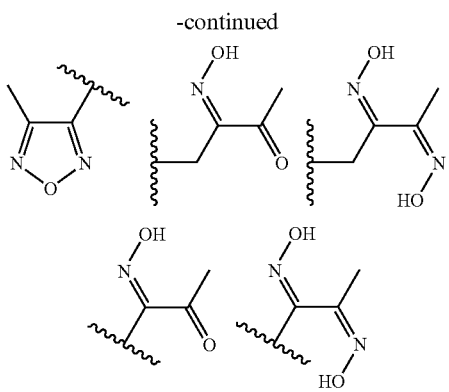

where Ph is phenyl.

The compounds also include the corresponding metal conjugates, and pharmaceutically acceptable salts of the compounds and metal conjugates. Metals which can be used in the metal conjugates include, for example, copper, paladium, nickel or platinum. Preferably the metal is copper, such as Cu(II).

In one embodiment, the compound of Formula (I) is defined wherein R is

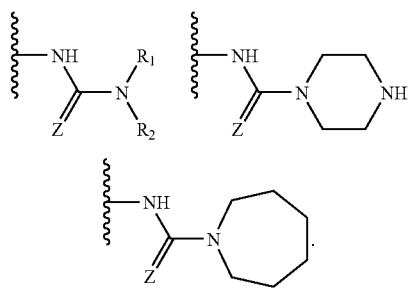

In another embodiment, the compound of Formula (I) is defined wherein R is

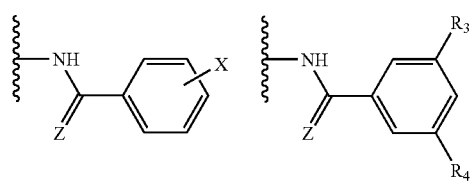

In still another embodiment, the compound of Formula (I) is defined wherein R is

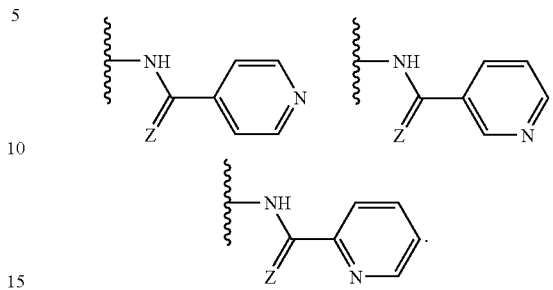

In yet another embodiment, the compound of Formula (I) is defined wherein R is

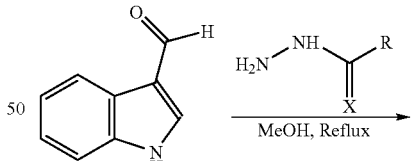

Exemplary compounds of the present invention include the Cu(II) complex of (2Z)-2-(N-hydroxyimino)-N'-[(1Z)-1H-indol-3-ylmethylidene]-1,3-dioxobutanehydrazide and the Cu(II) complex of 2-amino-3-[(Z)—N'-(1H-indol-3-ylmethylidene)hydrazinecarbonyl]-propanoic acid.

The compounds of the present invention may contain one or more stereocenters. The invention includes all possible diastereomers and all enantiomeric forms as well as all combinations of diasteriomers and enantiomers, including racemic mixtures. In addition, compounds of the present invention exist as tautomeric forms and all tautomeric forms are encompassed by the present invention. The compounds can be separated into substantially optically pure compounds.

Exemplary compounds of the invention can be prepared, for example, by the following general reaction scheme:

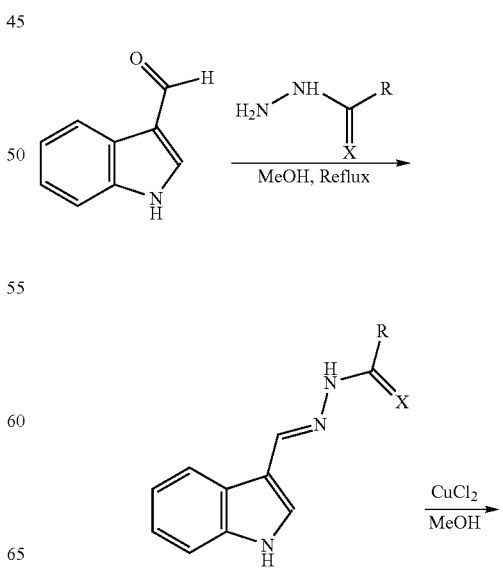

-continued

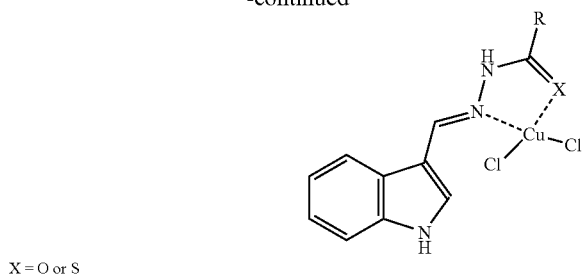

X = O or S

The Schiff base ligands are synthesized by mixing equimolar amounts of indole 3-carbaldehyde and corresponding hydrazides in methanolic solvent. The reaction mixture is refluxed for 1 h at reflux temperature. The methanol is removed under vacuum leading to completion of the reaction. The products obtained are washed with methanol to remove the unreacted indole 3-carbaldehyde. The products are recrystallized using methanol and dried over anhydrous $CaCl_2$. The copper(II) complexes are synthesized by mixing an equimolar amount of Schiff base ligand and $CuCl_2 \cdot 2H_2O$ in methanol. The resulting mixture is stirred at room temperature for 4 h. The precipitate is removed by filtration, washed with methanol, and dried over anhydrous $CaCl_2$.

Exemplary hydrazides used herein can be synthesized, for example, using following scheme:

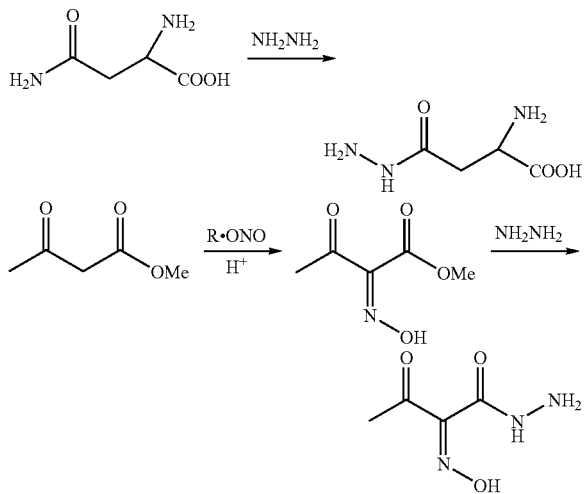

The hydrazides are utilized to synthesize the Schiff base ligands before obtaining the corresponding metal complexes.

The compounds of the present invention are useful in inhibition of serine/theonine protein kinase B (Akt). Thus, in one embodiment, the present invention provides a method for preventing or treating a disease, or a condition that predisposes to a disease, wherein the disease or condition is associated with activation of serine/threonine kinase B (Akt) in an animal. The method comprises administering to the animal a preventive or treatment effective amount of a compound of Formula (I).

Any disease or condition that predisposes to a disease which is associated with activation of serine/threonine kinase B (Akt) may be treated according to the methods of the present invention. Exemplary diseases and conditions that predispose to a disease are cancer and precancerous lesions, including breast cancer, lung cancer, ovarian cancer, uterine cancer, brain cancer, sarcoma, melanoma, leukemia, lymphoma, head and neck cancer, colorectal cancer, prostate cancer, pancreatic cancer, and liver cancer; a rheumatologic disease such as rheumatoid arthritis or osteoarthritis; a pulmonary disease such as chronic obstructive pulmonary disease (COPD); an opthalmic disease such as retinopathy; a cardiovascular disease; a dermatologic disease; a gynecological disease; a vascular disease; a neurologic disease; and an infectious disease such as a bacterial, viral, retroviral or parasitic disease.

When using a compound of Formula (I) for preventing or treating a disease, or a condition that predisposes to a disease, wherein the disease or condition is associated with activation of serine/threonine kinase B (Akt) in an animal, an additional compound effective for treating such a disease or condition may be administered with the compound of Formula (I). The additional compound may be administered before, after or simultaneously with the compound of Formula (I). For example, in the treatment of cancer, the compound of Formula (I) may be administered before, after or simultaneously with gemcitabine or a pharmaceutically acceptable salt thereof, capecitabine, erlotinib, gefitinib or cisplatin.

In another embodiment, the present invention relates to a method for increasing apoptosis of an animal cell comprising contacting the cell with a compound of Formula (I). For example, exposure to a compound of Formula (I) can induce apoptosis in a cancer cell and thereby result in treatment of cancer in a patient in need of such treatment.

The animals and cells treated according to the methods of the present invention preferably are mammals and mammalian cells. The methods can be used in any mammalian species, including human, monkey, cow, sheep, pig, goat, horse, mouse, rat, dog, cat, rabbit, guinea pig, hamster and horse. Humans are preferred.

The compounds of the present invention can be delivered directly or in pharmaceutical compositions along with suitable diluents, carriers or excipients, as is well known in the art. For example, a pharmaceutical composition of the invention may include a conventional additive, such as a stabilizer, buffer, salt, preservative, filler, flavor enhancer and the like, as known to those skilled in the art. Exemplary buffers include phosphates, carbonates, citrates and the like. Exemplary preservatives include EDTA, EGTA, BHA, BHT and the like.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences.

Suitable routes of administration may, for example, include oral, rectal, transmucosal, transdermal, topical, nasal, or intestinal administration and parenteral delivery, including intramuscular, subcutaneous, intramedullary injections, as well as intrathecal, direct intraventricular, intravenous, intraperitoneal, intranasal, or intraocular injections. In addition, the agent or composition thereof may be administered sublingually or via a spray, including a sublingual tablet or a sublingual spray. The agent or composition thereof may be administered in a local rather than a systemic manner. For example, a suitable agent can be delivered via injection or in a targeted drug delivery system, such as a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks' solution, Ringer's solution, or physiological saline buffer. For transmucosal or nasal administration, penetrants appropriate to the barrier to be permeated are used in the formulation. Such penetrants are generally known in the art. In a preferred embodiment of the present invention, the present compounds are prepared in a formulation intended for oral administration. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Also, wetting agents such as sodium dodecyl sulfate may be included.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In one embodiment, the compounds of the present invention can be administered transdermally, such as through a skin patch, or topically. In one aspect, the transdermal or topical formulations of the present invention can additionally comprise one or multiple penetration enhancers or other effectors, including agents that enhance migration of the delivered compound. Transdermal or topical administration could be preferred, for example, in situations in which location specific delivery is desired.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Formulations for parenteral administration include aqueous solutions or other compositions in water-soluble form.

Suspensions of the active compounds may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a depot preparation. Such long acting formulations may be administered by implantation (for example, subcutaneously or intramuscularly) or by intramuscular injection. Thus, for example, the present compounds may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for stabilization may be employed.

For any composition used in the present methods of treatment, a therapeutically effective dose can be estimated initially using a variety of techniques well known in the art. For example, in a cell culture assay, a dose can be formulated in animal models to achieve a circulating concentration range that includes the $IC_{50}$ as determined in cell culture. Dosage ranges appropriate for human subjects can be determined, for example, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein, and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

Example 1

Compound 1: Equimolar amounts of asparagine monohydrate and hydrazine hydrate were dissolved in water and heated to 100° C. until complete removal of ammonia gas. The hydrazide of asparagine thus generated was cooled and filtered. The Schiff base ligand was synthesized using this hydrazide and indole 3-carbaldehyde as described above. The compound was characterized by NMR. The Cu(II) complex was synthesized using the Schiff base ligand and CuCl2.2H2O as described above.

1H NMR (DMSO, D6) δ (ppm): 2.50 (2H, d, H10); 3.20 (1H, m, H11); 3.50 (2H, d, H12); 7.13 (2H, s, H5, H6); 7.35 (1H, s, H2); 7.40 (1H, d, H7); 8.08 (1H, d, H4); 8.27 (1H, s, H8); 8.80 (1H, s, H9); 11.18 (1H, s, H1); 11.68 (1H, s, H13).

Example 2

Compound 2: Methylacetoacetate (0.1 mol) and 0.3 ml of concentrated HCl were maintained at 40-50° C. with stirring. Butyl nitrite (0.1 mol) was slowly added while maintaining temperature at 40-50° C. for 30 min. The reaction was monitored by TLC. The mono-oxime was obtained by chilling the reaction mixture below 15° C. and neutralization with acid. Equimolar amounts of mono-oxime and hydrazine hydrate were dissolved in water and heated to 100° C. until complete removal of ammonia gas. The hydrazide of mono-oxime thus generated was cooled and filtered. The Schiff base ligand was synthesized using this hydrazide and indole 3-carbaldehyde as described above. The compound was characterized by NMR. The Cu(II) complex of this ligand was synthesized using Schiff base ligand and CuCl2.2H2O as described above.

1H NMR (DMSO, D6) δ (ppm): 2.56 (3H, s, H11); 7.17 (2H, s, H5, H6); 7.47 (1H, d, H7, J=6.9 Hz); 7.57 (2H, s, H2, H9); 8.39 (1H, d, H4, J=7.4 Hz); 8.90 (1H, s, H8); 11.04 (1H, s, H1).

Example 3

Cell Growth Inhibition by 3-(4,5-dimethylthiazol-2-yl)-2,5-diphenyltetrazolium Bromide Assay COLO 357 cells (K-ras mutated pancreatic cancer) were seeded at a density of $3 \times 10^3$ cells per well in 96-well microtiter culture plates. After overnight incubation, medium was removed and replaced with fresh medium containing different concentrations of compounds (0-100 μmol/L) diluted from a 10 mmol/L stock. On completion of 72 hours of incubation, 20 μL of 3-(4,5-dimethylthiazol-2-yl)-2,5-diphenyltetrazolium bromide (MTT) solution (5 mg/mL in PBS) were added to each well and incubated further for 2 hours. Upon termination, the supernatant was aspirated and the MTT formazan formed by metabolically viable cells was dissolved in 100 μL of isopropanol. The plates were mixed for 30 minutes on a gyratory shaker, and absorbance was measured at 595 nm using a plate reader (TECAN, Durham, N.C.). A similar protocol was used for BxPC3 (wild type K-Ras pancreatic cancer), PC3 (prostate cancer) and HCT (colon cancer) cell lines.

Example 4

Cell Growth Inhibition by Cytotoxic Agents

Cells were plated as described above and allowed to attach overnight. The cells were replaced with fresh medium containing 25 μmol/L of Compound 1 and Compound 2 for 72 hours. The effect of Compound 1 and Compound 2 pretreatment on cell viability was examined by the MTT assay method as described above.

Example 5

Quantification of Apoptosis by ELISA

The Cell Apoptosis ELISA Detection Kit (Roche, Palo Alto, Calif.) was used to detect apoptosis in COLO357 cells, with different treatments according to the manufacturer's protocol. Briefly, COLO357 cells were treated with 25 mmol/L of Compound 1 and Compound 2 for 72 hours. After treatment, the cytoplasmic histone DNA fragments from COLO 357 cells with different treatments were extracted and bound to immobilized anti-histone antibody.

Subsequently, the peroxidase-conjugated anti-DNA antibody was used for the detection of immobilized histone DNA fragments. After addition of substrate for peroxidase, the spectrophotometric absorbance of the samples was determined using ULTRA Multifunctional Microplate Reader (TECAN) at 405 nm. A similar protocol was used for BxPC3, PC3 and HCT116 cell lines.

Example 6

DNA Ladder Analysis for Detecting Apoptosis

COLO 357 cells were treated with 25 μmol/L of Compound 1 and Compound 2 for 72 hours. After treatment, cellular cytoplasmic DNA from COLO 357 cells with different treatments was extracted using 10 mmol/L Tris (pH 8.0), 1 mmol/L EDTA, and 0.2% Triton X-100. The lysate was centrifuged for 15 minutes at 13,000×g to separate the fragment DNA (soluble) from intact chromatin (nuclear pellet). The supernatant from the lysate was treated with RNase, followed by SDSProteinase K digestion, phenol chloroform extraction, and isopropanol precipitation. DNA was separated through a 1.5% agarose gel.

TABLE 1

MTT assay of VLife's compounds on four cell lines

| | MTT Assay EC50 after 72 h (μM) | | | |
|---|---|---|---|---|
| Compound | BxPC3 | COLO357 | HCT116 | PC3 |
| Compound 1 | 28.87 | 14.63 | 11.65 | 28.82 |
| Compound 2 | 18.88 | 14.30 | 14.08 | 16.58 |

TABLE 2

Apoptosis measures for compounds against control

| | O.D. Of Histone/DNA at 405 nm | | | |
|---|---|---|---|---|
| Compound | BxPC3 | COLO357 | HCT116 | PC3 |
| Control | 0.50 | 0.75 | 0.35 | 0.50 |
| Compound 1 | 2.20 | 1.90 | 1.60 | 0.60 |
| Compound 2 | 1.80 | 2.00 | 1.75 | 1.90 |

Example 7

Akt Assay

Akt activity kit is an ELISA based activity kit that utilizes biotinylated peptide substrate (GRPRTSSFAEG) that is phosphorylated on second serine by Akt1, Akt2, Akt3, SGK and MSK1. Biotinylated Akt substrate and sample containing Akt are incubated in presence of ATP in the wells of a streptavidin coated 96-well plate, which allows for phosphorylation and substrate capture in a single step. The phosphorylated substrate is detected using phosphoserine detection antibody followed by HRP-antibody conjugate and color development with TMB substrate. Sensitivity is increased by addition of ELISA stop solution and relative activity is determined by reading dual absorbance at 450/540 nm or 450/595 nm. Inhibition profiles can be generated based on Akt activity in the presence and absence of test inhibitor(s).

Both compound 1 and compound 2 show Akt inhibitory activity in the micromolar range.

Example 8

In-Vivo Model of Pancreatic Cancer

The orthotopic pancreatic cancer model of mice was created using PANC-1 cell line, which expresses aberrant Akt. Pancreatic tumor cells (Panc-1) ($1\times10^6$) were orthotopically injected into the pancreas of SCID mice. One month later upon confirmation of tumor growth, treatment was initiated by intravenous injection of Compound 2 (25 mg/kg body weight; 5 doses, given every third day). Mice were euthanized 10 days following the last dose of treatment.

It will be appreciated that, although specific embodiments of the invention have been described herein for purposes of illustration, various modifications may be made without departing from the spirit and scope of the invention. All such modifications and variations are intended to be included herein within the scope of this disclosure and the present invention and protected by the following claims.

We claim:

1. An indole-metal complex, wherein the indole is 2-amino-3-[(Z)—N'-(1H-indol-3-ylmethylidene)hydrazinecarbonyl]propanoic acid and the metal is copper (CuII).

2. A composition comprising the indole-metal complex of claim 1 and a pharmaceutically acceptable diluent, carrier or excipient.

3. A composition comprising an effective amount of the indole-metal complex according to claim 1 and an effective amount of a compound selected from the group consisting of gemcitabine capecitabine, erlotinib, gefitinib, cisplatin, and a pharmaceutically acceptable salt thereof.

* * * * *